United States Patent [19]

Jolles et al.

[11] 4,261,979

[45] Apr. 14, 1981

[54] NOVEL WATER-SOLUBLE COMPOUNDS DERIVED FROM EXTRACTS OF STREPTOMYCES STIMULOSUS, PROCESS FOR THEIR PRODUCTION, THEIR USES AS IMMUNOLOGICAL ADJUVANTS AND COMPOSITIONS CONTAINING THEM

[75] Inventors: Pierre Jolles, Paris; Jean Florent, Boulogne-Billancourt; Jean Lunel, Paris; Denise Mancy, Charenton; Daniele Migliore-Samour, Kremlin-Bicetre, all of France

[73] Assignee: Agence Nationale de Valorisation de la Recherche (ANVAR), Neuilly sur Seine, France

[21] Appl. No.: 84,927

[22] Filed: Oct. 15, 1979

[30] Foreign Application Priority Data

Oct. 19, 1978 [FR] France .................................. 78 29838
Oct. 5, 1979 [FR] France .................................. 79 24923

[51] Int. Cl.$^3$ ...................... C07C 103/52; A61K 37/00
[52] U.S. Cl. ................................ 424/177; 260/112.5 R
[58] Field of Search .................. 424/177; 260/112.5 R

[56] References Cited

FOREIGN PATENT DOCUMENTS

2833799 2/1979 Fed. Rep. of Germany ........... 424/177

Primary Examiner—Delbert R. Phillips
Attorney, Agent, or Firm—Sprung, Felfe, Horn, Lynch & Kramer

[57] ABSTRACT

The invention relates to novel water-soluble compounds, process for their preparation, methods of therapeutic treatment therewith and pharmaceutical compositions containing them. The compounds correspond to the formulae (III) and (IV) below or their mixtures in molar proportions of about 4/1, in which formulae X represents a RCO radical and Y represents a hydrogen atom or a RCO radical, or again in which Y represents a RCO radical and X represents a hydrogen atom or a RCO radical, R being an alkyl or alkenyl radical containing 11 to 19 carbon atoms in a straight or branched chain.

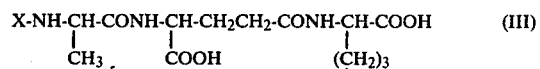

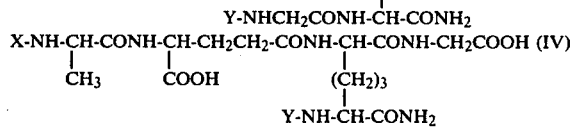

The compounds are useful as immunological adjuvants.

9 Claims, 3 Drawing Figures

NOVEL WATER-SOLUBLE COMPOUNDS DERIVED FROM EXTRACTS OF STREPTOMYCES STIMULOSUS, PROCESS FOR THEIR PRODUCTION, THEIR USES AS IMMUNOLOGICAL ADJUVANTS AND COMPOSITIONS CONTAINING THEM

The present invention relates to novel compounds possessing utility as immunological adjuvants, more particularly compounds derived from a water-soluble extract of *Streptomyces stimulosus* DS 25556 (NRRL 5776), to the process for their preparation, to the methods of medical treatment of humans or animals therewith and to the pharmaceutical compositions containing them.

More precisely, the novel compounds according to the invention are derived from the coupling with long chain aliphatic acids of the substances corresponding to the formulae (I) and (II) below, either alone or in admixture in a molar ratio of about 4/1:

where the amino acids have the following configurations: Ala:L Glu:D Dap:LL.

The compounds according to the present invention are hence constituted from the water-soluble extract of *Streptomyces stimulosus DS* 25556 (NRRL 5776), coupled with long chain aliphatic acids, said compounds corresponding to the following general formulae (III) and (IV), or consisting of a mixture in molar ratio of about 4 to 1 of said compounds:

in which X represents a RCO radical and Y represents a hydrogen atom or a RCO radical, or again in which Y represents a RCO radical and X represents a hydrogen atom or a RCO radical, it being understood that, in these definitions R represents an alkyl or alkenyl radical containing 11 to 19 carbon atoms in a straight or branched chain and in which the amino acids have the previously indicated configurations.

These compounds are themselves substantially water-soluble.

In the present description, by the expression "compounds of the invention" is meant the compounds corresponding to the above specified general formulae (III) and (IV), considered singly or in admixture in a respective molar proportion of about 4/1.

In the same way, by the expression "starting materials" is meant the products corresponding to the specified general formulae (I) and (II) considered alone or in admixture in a respective molar proportion of about 4/1.

According to the invention, the claimed compounds can be obtained by the action of an active derivative of an aliphatic acid of the general formula:

in which R is as previously defined (for example lauric acid), on one of the materials (tetrapeptides) of formula (I) or (II) or their mixture. It is particularly advantageous to use as the active derivative of the acid (V) its anhydride, in a peptide/anhydride ratio close to 1/5. In this case, the operation is carried out in a water-miscible organic solvent, such as tertiary butyl alcohol, at a temperature comprised between 15° and 35° C., preferably at a temperature close to 20° C., in the presence of a base such as sodium carbonate in aqueous solution.

The compounds according to the invention are then isolated from the reaction medium, for example, by precipitation, evaporation of the solvents or by any other suitable means.

The novel compounds of the present invention can be purified if necessary by currently used physical methods for purification, such as precipitation, dialysis, chromatography, filtrations on various supports used for this purpose.

The starting materials can be obtained by successive purifications of an extract denoted under the number 34129 R.P., of *Streptomyces stimulosus* DS 25556 (NRRL 5776), by means of chromatography over various supports used for this purpose. It is generally carried out in a very slightly acid aqueous solvent, for example 0.01 N acetic acid solution. By carrying out successive chromatographies on supports such as the "Biogels", the mixture of products (I) and (II) is generally obtained in the molar ratio of about 4/1. It is possible to separate the tetrapeptides of formula (I) and (II) by known means, for example by subjecting the mixture to chromatography over a Dowex 50X 4 column, and by eluting with suitable mixtures of solvents of decreasing acidity. As elution solvent, it is particularly advantageous to use a pyridineacetic acid-water mixture whose pH has been adjusted to the desired value by the addition of formic acid. Also in such a system, the tetrapeptide of formula (I) is eluted when the pH reaches 4.1.

Each of the tetrapeptides thus-obtained is desalted by filtration over a "Biogel P2" column and eluting with 0.01 M acetic acid.

The structures of the starting materials have been determined by means of a study of the dipeptides obtained by partial acid hydrolysis as well as by mass spectrometry. The two N-terminal acids, Ala and Gly, have been established by the conventional methods of Edman and dansylation. The absence of aminated or unaminated reducing sugars has been checked by gas phase chromatography.

Figure 3:
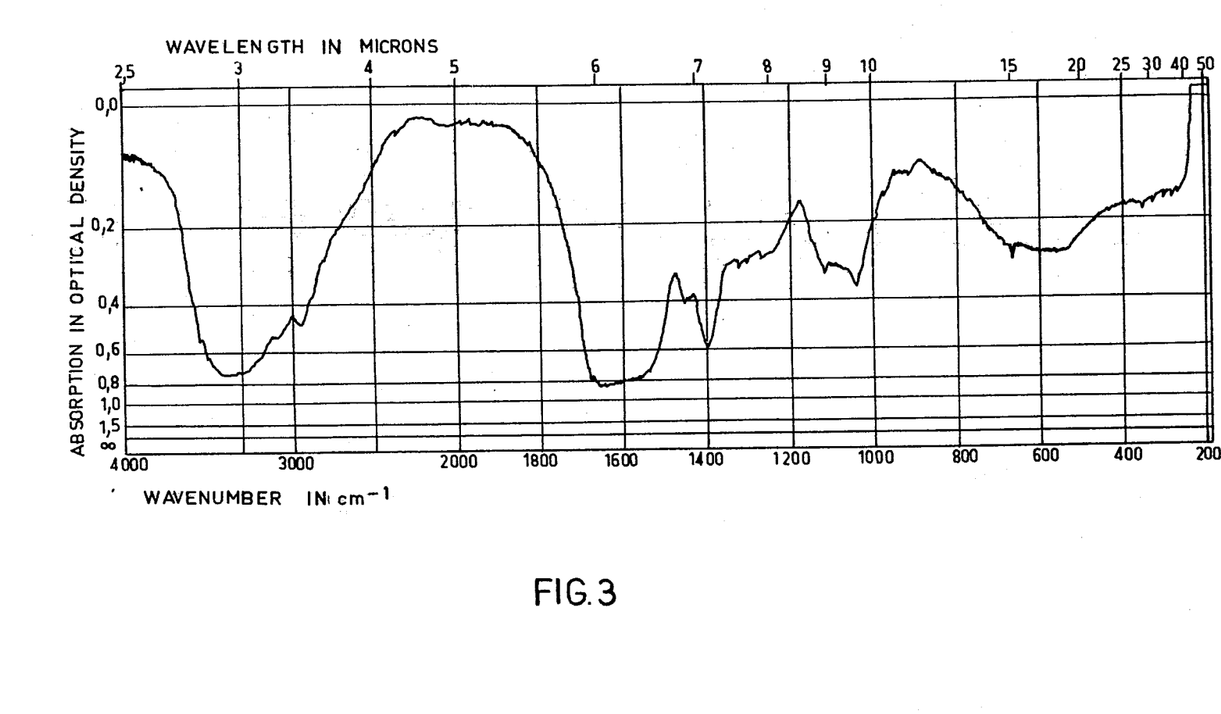

The extract of *Streptomyces stimulosus* DS 25556 (NRRL 5776) denoted by the number 34129 R.P. has the following essential characteristics:

appearance: amorphous cream powder (after lyophilization)

composition:
  (a) of amino acids: alanine (5 to 7%), glutamic acid (7 to 10%), glycine (2.5 to 4%), $\alpha,\alpha$-diaminopimelic acid (5 to 8%),
  (b) of amino sugars: N-acetylglucosamine (5 to 10%), muramic acid (5 to 10%)

elementary analysis:
C%=40.4–41.4 H%=6.7–6.9 N%=8.0–10.6 infra-red spectrum: (determination from tablets in admixture with KBr).

This spectrum is represented by the FIG. 3 appended in which there are drawn as abscissae, on the one hand, the wave lengths expressed in microns (upper scale) and on the other hand, the number of waves in $cm^{-1}$ (lower scale), and as ordinates, the optical densities.

In the Table I below are indicated the principal infrared absorption bands of the 34129 R.P. extract expressedin wave number ($cm^{-1}$).

TABLE I

| 3400 H$_2$O | 1320 w |
|---|---|
| 3300 sh. | 1260 m |
| 3100 sh. | 1140 sh. |
| 2970 m | 1115 m |
| 2950 m | 1075 sh. |
| 2880 sh. | 1040 S |
| 2600 sh. | 975 sh. |
| 2060 vw | 910 w |
| 1650 vS | 855 sh. |
| 1590 vS | 770 sh. |
| 1450 m | 720 sh. |
| 1400 S | 690 sh. | vS = very strong
vw = very weak
m = medium
S = strong
w = weak
sh. = shoulder.

The process of preparation of the water-soluble extract 34129 R.P. comprises the steps of:

subjecting delipidated cells of *Streptomyces stimulosus* DS 25556 to repeated autolyses and then of fractionating the water-soluble part by filtration through supports of suitable porosity in order to obtain substances whose molecular weight is comprised between 2000 and 20,000.

The micro-organism *Streptomyces stimulosus* DS 25556 has been isolated from a soil sample obtained in India. The isolation was carried out according to the general method which consists in placing a small amount of soil in suspension in water at different concentrations, and in spreading a small volume of each dilution over the surface of Petri dishes containing a gelose nutrient medium. After incubation for some days at 6° C., which permits the micro-organism to develop, the colonies which it is desired to isolate to pursue the study are taken up and reinjected on nutrient geloses in order to obtain more abundant cultures therefrom.

A specimen of this strain was deposited at the Northern Regional Research Laboratory of the U.S. Department of Agriculture at Peoria, Ill. (United States of America) where it was recorded under the reference NRRL 5776. This laboratory is irrevocably authorized to distribute this strain to any person legally having knowledge of the present document.

*Streptomyces stimulosus* DS 25556 forms cylindrical spores measuring 0.6 to 0.8$\mu$/1.0 to 1.3$\mu$. The sporifer chains, straight or slightly flexed, are generally long and include mostly several tens of spores; the sporophores are simple or have some branches in clusters. By its mode of sporulation, this strain is classed in the section Rectus-Flexibilis of the Pridham classification.

*S. stimulosus* DS 25556 has a sporulated aerial mycelium gray in color. It develops well at 26° C., badly at 37° C. and not at all at 50° C.

It gives an abundant production of dark melanic pigment on organic media, and in particular on the special gelose tyrosine—yeast extract of Waksman (Melanin formation medium") see "ref. F" mentioned below; in addition, in certain cases, it also gives more or less abundantly, a soluble pigment ranging from violet-blue to red according to the degree of acidity of the medium to which it is capable of communicating its color. The latter pigment is produced in particular abundance on gelose with calcium malate, which takes up a very characteristic intense violet-blue color.

In cultures carried out at 26° C., it has the following biochemical characteristics:

| - melanine production | : positive |
|---|---|
| - H$_2$S production | : positive |
| - tyrosinase | : positive |
| - gelatine liquefaction | : positive |
| - utilization of cellulose | : positive |
| - production of nitrites from nitrates | : positive on synthetic media as well as on nitrate nutrient broth |
| - starch hydrolysis | : positive |
| - culture on milk | : peptonization without coagulation- with alkalinisation of the pH which passes from 6.3 to 7.8 in one month |

The culture characteristics of *Streptomyces stimulosus* DS 25556 are gathered in the table below. These are those of cultures which have reached a good stage of development, that is to say of about two to three weeks at 26° C. except for indications to the contrary. These characteristics have been observed on nutrient geloses and broths customarily used to determine the morphological characteristics of streptomyces strains, the cultures on gelose media being carried out on inclined geloses. A certain number of the culture media employed were prepared according to the formulae indicated in "The Actinomycetes", S.A. WAKSMAN, p. 193–197, Chronica Botanica Company, Waltham, Mass., U.S.A. 1950; in this case, they are indicated by the letter W followed by the number which has been attributed to them in "The Actinomycetes". The references or constitutions of the other culture media are as follows:

—Ref. A—"Hickey and Tresner's Agar"—T. G. PRIDHAM et al.—Antibiotics Annual, 1956-1957, p. 950

—Ref. B—"Bennett's Agar"—S. A. WAKSMAN—The Actinomycetes, vol. 2, p. 331, No. 30—The Williams and Wilkins Company, Baltimore, 1961.

—Ref. C—Formula W-23, supplemented with 2% of gelose

—Ref. D—"Yeast Extract Agar"—T. G. PRIDHAM et al Antibiotics Annual, 1956-1957, p. 950

—Ref. E—"Tomato Paste Oatmeal Agar"—T. G. PRIDHAM et al.—Antibiotics Annual, 1956-1957, p. 950

—Ref. F—"Melanin formation medium"—S. A. WAKSMAN—The Actinomycetes, vol. 2, p. 333, No. 42—The Williams and Wilkins Company, Baltimore, 1961

—Ref. G—W. E. GRUNDY et al.—Antibiotics and Chem. 2 401, 1952.

—Ref. H—"Inorganic Salts"—Starch Agar"—T. G. PRIDHAM et al—Antibiotics Annual, 1956-1957, p. 951

—Ref. I—"Medium 1 with a mineral source of nitrogen" G. F. GAUZE et al—Problems in the classification of Antagonistic Actinomycetes—p. 13—The American Institute of Biological Sciences, Washington 6, D.C. 1959.

—Ref. J—corresponds to the formula W-1, where 30 g of saccharose are replaced by 15 g of glucose —Ref. K—corresponds to the formula W-1, wherein 30 g of saccharose are replaced by 15 g of glycerine —Ref. L—"Manual of Methods for Pure Culture Study of Bacteria"—Society of American Bacteriologists, Geneva, N.Y.—$II_{50}$—19

—Ref. M—corresponds to the formula W-18, wherein the saccharose is eliminated and replaced by small strips of filter paper partially immersed in the liquid —Ref. N—"Manual of Methods for Pure Culture Study of Bacteria"—Society of American Bacteriologists, Geneva, N.Y.—$II_{50}18$ —Ref. P—"Plain gelatine"—prepared according to the indications of the "Manual of Methods for Pure Culture Study of Bacteria"—Society of American Bacteriologists, Geneva, N.Y.—$II_{50}$—18

—Ref. Q—Commercial powdered skimmed milk, reconstituted according to the manufacturer's instructions —Ref. R—Medium indicated for research into the production of $H_2S$ by: H. D. TRESNER and F. DANGA—Journal of Bacteriology, 76, 239-244, 1958.

| Culture Media | Degree of Development | Vegatative mycelium or Reverse side of the Culture | Aerial apparatus (comprising the whole of the aerial mycelium and of the sporulation | Soluble Pigment | Observations and biochemical properties |
| --- | --- | --- | --- | --- | --- |
| Gelose of Hickey and Tresner (Ref. A) | Good | Reverse brown-black | Dark gray | Black, abundant | Cylindrical spores measuring 0.6 to 0.8 μ/1.0 to 1.3 μ Straight sporifer chains including several ten's of spores. Simple sporophores or with some branching into clusters |
| Gelose of Bennet (Ref. B) | Good | Reverse deep maroon | Violet-gray | Very dark brown | |
| Gelose of Emerson (Ref. C) | Good | Reverse very deep yellow-brown | Gray | Blackish brown | |
| Gelose with yeast extract of Pridham (Ref. D) | Good | Reverse deep yellow-brown to black-brown | Light violet-gray to dark gray | Blackish brown | |
| Gelose with oat flour and tomatoe extract of Pridham (Ref. E) | Good | Reverse deep yellow-brown | Dark gray | Dark brown | |
| Glucose-Peptone gelose (W-7) | Good | Reverse blackish brown | Dark-gray | Black-brown | |
| Nutrient gelose (W-5) | Fairly Good | Reverse yellow-brown | Light-gray | Blackish brown | |
| Tyrosine-yeast extract gelose for melanine formation (Ref. F) | Fairly Good | Reverse blackish brown | Light pink-colored gray | Abundant black | Production of melanine positive (readings made according to the author's recommendations). |
| Gelose with calcium malate of Krainsky (Ref. G) | Moderate | Reverse violet | Gray-moderately developed | Abundant violet-blue | Solubilization of the malate positive but slow |
| Gelose with ovalbumin (W-12) | Poor | V.M. colorless to orange-colored gray: Very poorly developed | Grayish in the state of traces | Weak orange colored gray | |
| Glucose asparagin | Moderate | Reverse orange-colored brown | Whitish to gray Very moderately | Weak orange colored | |

-continued

| Culture Media | Degree of Development | Vegatative mycelium or Reverse side of the Culture | Aerial apparatus (comprising the whole of the aerial mycelium and of the sporulation | Soluble Pigment | Observations and biochemical properties |
|---|---|---|---|---|---|
| gelose (W-2) | | | developed | pink | |
| Glycerine-asparagin gelose (W-3) | Fairly Good | Reverse orange-colored brown | Pink-colored white to gray Moderately developed | Brownish red | |
| Starch-mineral salts gelose of Pridham (Ref. H) | Good | Reverse brown-yellow | Yellowish gray | Grayish yellow-brown | Hydrolysis of starch: positive Cylindrical spores measuring 0.6 to 0.8 $\mu$/ 1.0 to 1.3 $\mu$, Sporifer chains straight including several ten's of spores. Simple sporophores or with some branchings in clusters |
| Gelose starch nitrate (W-10) | Medium | Reverse yellow-brown to blackish brown | Light gray to dark gray | Brown-gray | Hydrolysis of starch: positive |
| Gelose with mineral source of nitrogen of Gauze (Ref. I) | Good | Reverse deep violet | Dark gray | Dark grayish violet | |
| Synthetic gelose of Czapek with saccharose (W-1) | Almost nil | V.M. little developed | Grayish white in the state of traces | Nil | |
| Synthetic gelose of Czapek with glucose (Ref. J) | Fairly Good | Reverse yellow-brown | Whitish to gray Moderately developed | Dark brown | |
| Synthetic gelose of Czapek with glycerine (Ref. K) | Fairly Good | V.M. thick and wrinkled, cracking, fairly dark orange-brown Reverse dark orange-colored brown | Whitish to gray very moderately developed | Dark orange colored brown | |
| Starch - nitrate broth (W-19) | Good | Thick web-Reverse dark brown | Dark gray | Brown, in small amount from the surface | Formation of nitrites: positive |
| Glucose-nitrate broth of Dimmick (Ref. L) | Moderate | Slight grayish white web | Nil | Nil | Formation of nitrites: positive |
| Czapek broth with cellulose (Ref. M) | Medium | Slight whitish web | Light grayish Very moderately developed | Nil | Formation of nitrites: positive Utilization of cellulose: positive |
| Difco nitrated nutrient broth (Ref. N) | Medium | Brownish web | Light gray to gray Moderately developed | Light brown | Formation of nitrites; positive |
| Cultivation on potatoe (W-27) | Very Good | V.M. thick and wrinkled orange colored brown to a very deep redish brown, going towards blackish | Whitish to gray Moderately developed | Black | |
| 12% pure gelatine (Ref. P) | Good | V.M. yellow-brown | Whitish to grayish in the state of traces | Yellow-brown | Liquefaction: positive, good |
| Skimmed Milk (Ref. Q) | (1) at 25° C. Good (2) at 37° C. Very Moderate | Yellow-brown ring Poorly developed deep brown ring | Grayish white In the state of traces Nil | | Peptonization without coagulation pH passing from 6.3 to 7.8 in one month Petonization without coagulation pH passing from 6.3 to 8.0 in one month |
| Tresner and Danga gelose (Ref. R) | Good | V.M. blackish brown | Grayish white In the state of traces | Abundant black | Production of $H_2S$ positive (readings carried out |

| Culture Media | Degree of Development | Vegatative mycelium or Reverse side of the Culture | Aerial apparatus (comprising the whole of the aerial mycelium and of the sporulation | Soluble Pigment | Observations and biochemical properties according to the author's recommendations) |
|---|---|---|---|---|---|

V.M. = Vegetative mycelium

*Streptomyces stimulosus* DS 25556 has a group of characteristics which does not coincide exactly with any of those of the strains already described, and this is why it must be considered as a novel species.

Considering the species whose description is given in "The Actinomycetes" (vol. 2, S. A. WAKSMAN, The Williams and Wilkins Company, Baltimore, 1961), as well as in Bergey's Manual of Determinative Bacteriology (7th edition, The Williams and Wilkins Company, Baltimore, 1957), the two species to which it approaches most closely are two species described in "The Actinomycetes": *Streptomyces phaeopurpureus* and *Streptomyces purpureofuscus;* like them, in fact, *S. stimulosus* DS 25556 forms melanic pigments on organic media, gives on the majority of media a vegetative mycelium going from yellow-brown or deep orange-coloured brown to black-brown, and on potato develops a vegetative mycelium which is orange-coloured brown to reddish-brown showing a moderately developed aerial mycelium ranging from whitish to gray. However, it cannot be recognized as identical with any of these two species since, on the one hand, *S. phaeopurpureus* forms spherical to elliptical spores, gives a good growth on synthetic gelose of Czapek with saccharose (nitrate agar saccharose), does not utilize cellulose, does not reduce nitrates and utilizes rhamnose, whilst *S. stimulosus* DS 25556 forms cylindrical spores, gives a practically non-existent growth on the synthetic gelose of Czapek with saccharose, utilizes cellulose, considerably reduces the nitrates and does not use rhamnose; on the other hand, *S. purpureofuscus* gives good growth on synthetic gelose of Czapek with saccharose, a colorless vegetative mycelium and a reddish-brown to deep wine brown soluble pigment on nutrient gelose, a purple soluble pigment on potato, a yellowish-green soluble pigment on gelatine, coagulates milk and does not utilize cellulose, whereas *S. stimulosus* DS 25556 gives practically non-existent growth on synthetic gelose of Czapek with saccharose, a brown-yellow vegetative mycelium and a blackish-brown soluble pigment on nutrient gelose, a black and not purple soluble pigment on potato, a brown-yellow without green shade soluble pigment on gelatin, does not coagulate milk and utilizes cellulose.

If, in addition, the species described by G. F. GAUZE et al (Problems in the classification of Antagonistic Actinomycetes—The American Institute of Biological Sciences, Washington, 1959), are considered, it is observed that *S. stimulosus* DS 25556 is classed in the "Violaceus" series which is characterized by the formation of a gray aerial mycelium and of a violet-blue to reddish-brown vegetative mycelium on "media with a mineral nitrogen source of Gauze". In this series, the two strains which could be considered similar through the violet color of its vegetative mycelium on "a medium with a mineral nitrogen source of Gauze" and its method of sporulation, are *Act. violaceorectus* and *Act. prunicolor*. However, *Act. violaceorectus* forms on gelose with starch a vegetative mycelium and a violet soluble pigment, on potato a vegetative mycelium and a violet-red soluble pigment, and in addition does not utilize cellulose and does not reduce nitrates, whereas *S. stimulosus* DS 25556 forms on gelose with starch a brown-yellow to blackish-brown vegetative mycelium and a gray-brown soluble pigment, on potato an orange coloured brown to reddish-brown vegetative mycelium and a black soluble pigment, and in addition utilizes cellulose and strongly reduces nitrates. For its part *Act. prunicolor*, contrary to *S. stimulosus* DS 25556, does not use cellulose, does not reduce nitrates, and lastly forms a violet pigment which is not soluble in the gelose medium and consequently cannot be compared with the violet soluble pigment produced by *S. stimulosus* DS 25556.

The capacity of *S. stimulosus* DS 25556 to utilize various sources of carbon and of nitrogen to ensure its development has been determined according to the principle of the method of Pridham and Gottlieb (J. of Bact. 56, 107-114, 1948); the degree of development was observed on the basic medium indicated by the authors, either the glucose by various sources of carbon respectively tested, or the $(NH_4)_2 SO_4$ by the various sources of nitrogen respectively tested. The results are indicated in the following table:

| Sources of carbon tested | Utilization | Sources of Nitrogen tested | Utilization |
|---|---|---|---|
| D-ribose | negative | Na NO$_3$ | positive |
| D-xylose | positive | Na NO$_2$ | positive |
| L-arabinose | positive | (NH$_4$)$_2$SO$_4$ | positive |
| L-rhamnose | negative | H(NH$_4$)$_2$PO$_4$ | positive |
| D-glucose | positive | Adenine | positive |
| D-galactose | positive | Adenosine | positive |
| D-fructose | negative | Uracil | negative |
| D-mannose | positive | Urea | positive |
| L-sorbese | negative | L-asparagin | positive |
| lactose | positive | glycocol | positive |
| maltose | positive | sarcosin | negative |
| saccharose | negative | DL-alanine | positive |
| trehalose | negative | DL-valine | positive |
| cellobiose | positive | DL-aspartic acid | positive |
| raffinose | negative | L-glutamic acid | positive |
| dextrine | positive | L-arginine | positive |
| inuline | negative | L-lysine | positive |
| amidon | positive | DL-serine | positive |
| glycogene | positive | DL-threonine | positive |
| glycerol | positive | taurine | negative |
| erythritol | negative | DL-phenylalanine | positive |
| adonitol | negative | L-tyrosine | positive |
| dulcitol | negative | DL-proline | positive |
| D-mannitol | negative | L-hydroxyproline | positive |
| D-sorbitol | negative | L-histidine | positive |
| inositol | negative | L-tryptophane | positive |
| salicine | positive | betaine | negative |

The process of preparing cells of *Streptomyces stimulosus* comprises the steps of cultivating *Streptomyces stimulosus* DS 25556 (NRRL 5776) on a suitable medium and under suitable conditions and of separating the cells which have multiplied within the culture.

The culture of *Streptomyces stimulosus* DS 25 556 may be carried out by any aerobic culture method at the surface or in depth, but the latter is to be preferred for reasons of convenience. To this end, various types of equipments are used which are conventional in the fermentation industry.

In particular the following sequence can be adopted for conducting the operations:

The fermentation medium must contain essentially a source of assimilable carbon and a source of assimilable nitrogen, mineral elements, in particular sulfates, and if necessary growth factors, all these elements being introduced in the form of well-defined products or in complex mixtures, such as are encountered in biological products of various origin.

As sources of assimilable carbon it is possible to use carbohydrates, such as glucose, maltose, dextrins, starch or other carbon-containing substances such as sugar-alcohols (glycerol) or such as certain organic acids (lactic, citric acids).

Certain animal or vegetable oils such as lard oil or soya oil may advantageously replace these various carbon sources or be added to them.

Suitable sources of assimilable nitrogen are extremely varied. They may be very simple chemical substances such as mineral or organic salts of ammonium, urea, or certain amino acids. They may also be introduced by complex substances containing principally nitrogen in protein form such as casein, lactalbumin, gluten and their hydrolysates, flours of soya, of peanuts, of fish, meat extracts, yeast extracts, distiller solubles, infusions of cereals (notably corn steep).

Among the mineral elements added, certain may have a buffer or neutralizing effect such as the alkali or alkaline-earth phosphates or the carbonates of calcium and of magnesium. Others contribute the ionic equilibrium necessary to the development of *Streptomyces stimulosus* DS 25556 such as chlorides and sulfates of alkaline and alkaline-earth metals. Finally, certain substances act more especially as activators of the multiplication of the cells: these are zinc, cobalt, iron, copper, or manganese salts.

The pH of the starting fermentation medium of the culture must be comprised between 6.0 and 7.8 and preferably between 6.5 and 7.8. The optimum temperature for the fermentation is 25° to 30° C., but a satisfactory production is obtained at temperatures comprised between 23° and 33° C. The aeration of the fermentation can vary between rather wide values. It has however been found that aerations of 0.3 to 3 liters of air per liter of broth and per minute are particularly appropriate. The maximum yield is obtained after 2 to 8 days of culture, this time depending essentially on the medium used.

In accordance with the foregoing, it is understood that the general conditions of the culture of *Streptomyces stimulosus* DS 25556 can vary within a fairly wide extent and be adapted to each particular necessity.

The cells of *Streptomyces stimulosus* are separated from the fermentation medium by centrifugation. Generally, this operation is carried out continuously. The cells thus obtained can be purified and partially delipidated by successive washings by means of an organic solvent such as methanol, ethanol or ethyl ether or by a mixture of these solvents.

The cells of *Streptomyces stimulosus* DS 25556 are delipidated according to the conventional methods that is to say by successive washings by means of an organic solvent such as methylene chloride, chloroform or carbon tetrachloride.

Generally, in the course of each washing, the cells are shaken in the chloroform at a temperature of about 20° C. for 15 to 35 hours.

After each washing, the cells are filtered and dried under reduced pressure at a temperature comprised between 25° and 45° C.

The delipidated cells thus obtained are subjected to several successive autolysis at a temperature of about 37° C. for about 48 hours. It is particularly advantageous to operate in the presence of an agent capable of avoiding interfering fermentations. Preferably, benzene or toluene is used.

Each autolysis is carried out by shaking the delipidated cells slowly in water suspension. After each operation, the clear aqueous phase is separated from the solid phase by centrifugation and the following autolysis operation is carried out on the centrifugation cake. Generally, it is advantageous to carry out two to three autolysis operations.

The combined clear aqueous phases, which contain the 34129 R.P. extract are then fractionated by filtration through suitable supports. Preferably, in order to carry out this separation, membranes of suitable porosity are used, such as the AMICON UM 20 membrane and the AMICON UM 2 membrane.

Generally ultrafiltration of the clear aqueous phase is carried out first through a membrane enabling separation of products of high molecular weight and then the permeate obtained is ultrafiltered through a membrane which permits the separation of the substances of low molecular weight, the extract 34129 R.P. being contained in the retentate from this ultrafiltration. By lyophilization of this retentate the water-soluble extract 34129 R.P. is obtained.

The compounds according to the invention, that is to say derived from the coupling with fatty acids of the "starting materials", themselves obtained by purification of the water soluble extract 34129 R.P., are immunological adjuvants exerting their potentiating activity on antibody production and on delayed hypersensitivity reactions. They are non-arthrogenic, capable of exerting their adjuvant activity in aqueous solution or suspension, without the need to administer them in oily solution. When administered in aqueous solution, they exert a significant adjuvant power, distinctly more marked than that of the uncoupled water-soluble extracts from which they are derived. This adjuvant power is determined by tests of hypersensitivity and of antibody production in the guinea pig using as antigen, for example, ovalbumin (according to the principle of the method of R. G. WHITE et al. Immunology, 7, 158 (1964)). The adjuvant power in the guinea pig is exerted at doses comprised between 0.01 and 0.5 mg/kg. The compounds according to the invention exert, in vitro, at concentrations of 0.1 to 100 µg/cm³ a mitogenic activity on the spleenic lymphocytes of the mouse.

The compounds according to the invention are shown to be also active in the technique of JERNE in the mouse when, administered by the intravenous route at doses comprised between 0.1 and 25 mg/kg, they exert a stimulant effect on the production of antibody-forming cells in the spleen.

In all these respects, the compounds resulting from the coupling with lauric anhydride have proved to be interesting. The compound of formula (III) is particularly preferred. It will be noted that in the compound of formula (III), X and Y can be the same or different and represent either both a RCO radical or a RCO radical and the other a hydrogen atom, so that the compound (III) can be a single compound or a mixture. In the following the expression "compound (III)" covers both said mixture or its individual constituents.

The following example, is given by way of non-limiting illustration and embodiment of the present invention.

Figure 1:
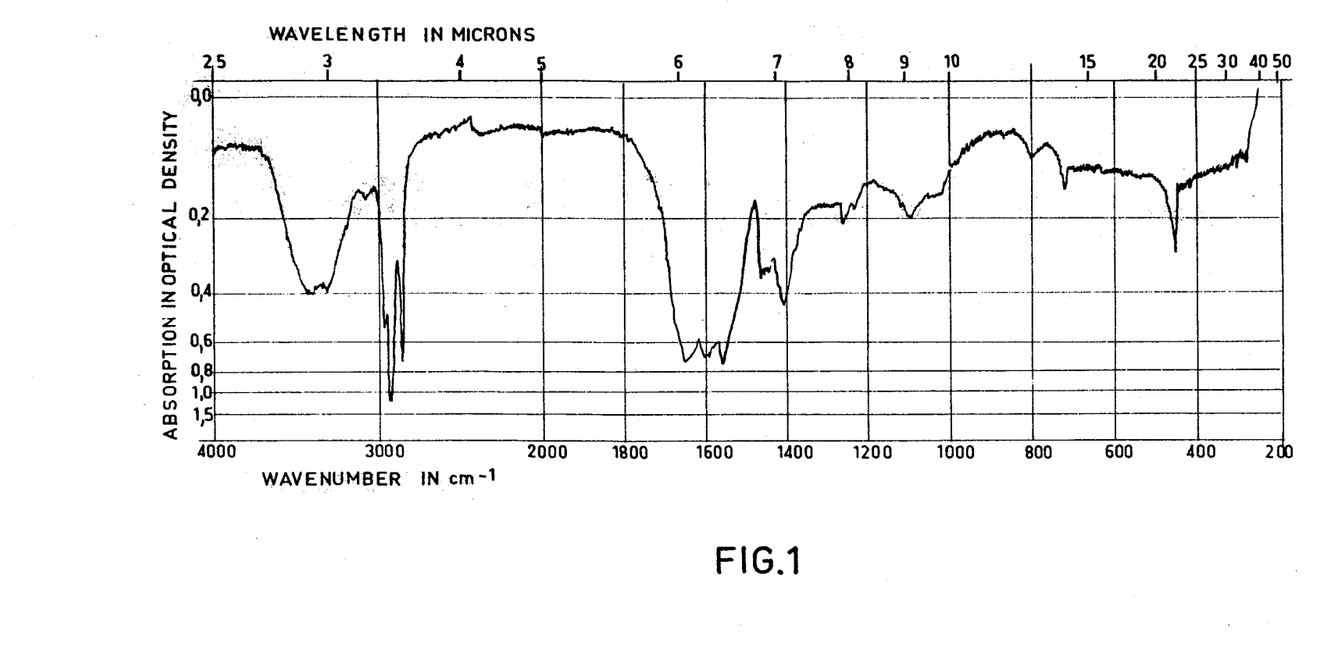

EXAMPLE 15 mg of the product of formula (I) are dissolved in 5 cm³ of a mixture of an 0.5 M aqueous solution of sodium carbonate and tertiary butyl alcohol (7/3 by volume). Drop by drop, with stirring and at a temperature close to 20° C., 0.5 cm³ of tertiary butyl alcohol containing 60 mg of lauric anhydride are added. After having stirred for 30 minutes, the tertiary butyl alcohol is added until a tertiary butyl alcohol level of 80% is reached. A precipitate is then formed which is separated by centrifugation (3000 rpm for 10 minutes). The precipitate is washed twice with 10 cm³ of tertiary butyl alcohol and then centrifuged each time under the same conditions as above. All the supernatant liquors of centrifugation are combined and concentrated to dryness in a rotary evaporator under reduced pressure (20 mm of mercury) at a temperature below 30° C. The evaporation residue is taken up again with 50 cm³ of distilled water and dialysed through a Diaflo (AMICON) UM-05 membrane, in order to remove the major part of the lauric acid arising from the hydrolysis of the unreacted lauric anhydride. The solution which has not dialysed is freeze-dried. In this way 30 mg of an amorphous white powder containing again 10% of lauric acid is obtained. 30 mg of said powder are filtered on Spherosil XOA-400 (which is a resin based on silica in porous spherical particles of a granulometry comprised between 100 and 200 microns, the porous volume of which is 1 ml/g and the pore diameter approximately 80 angstroms, marketed by Rhone Poulenc Industries), in a column of 25×1 cm in chloroform-methanol-water (75/25/2) solvent. The lauric acid is eluted in the dead space of the column and the compound (III) is eluted by the tertiary butanol-water (50/50) mixture. The relative composition of the amino acids in compound (III), determined by an auto-analyser after total hydrolysis, is the following (between parentheses is indicated the closest whole number in accordance with the experiment carried out after different periods of hydrolysis):

Ala=1.08 (1); Glu: 0.79 (1); Gly=1.0 (1); Dap=0.83 (1). The infrared spectrum of this substance is represented by FIG. 1.

The starting material of formula (I) can be prepared in the following manner:

300 mg of 34129 R.P. extract (extracts of *Streptomyces stimulosus*) are dissolved in 2 cm³ of 0.01 N aqueous acetic acid solution. The solution is filtered on a column of 2.40 m height and 2 cm diameter filled with Biogel P 10 (Biorad) by eluting with 0.01 N acetic acid. The desired substance is eluted between 400 and 550 cm³. It is filtered again on a column identical with the preceding one by still eluting with an 0.01 N aqueous acetic acid solution. After having removed a first fraction of 170 cm³, the eluate passing between 200 and 230 cm³ is collected. This eluate is passed successively over two columns of 2.40 m height and 1.2 cm diameter filled respectively with "Biogel P 4" and "Biogel P 2" by eluting with an 0.01 N aqueous acetic acid solution. After having eluted the last column with 135 cm³ of elution solvent, the fraction coming out between 135 and 140 cm³ is collected; this latter, after lyophilization, provides 15 mg of a mixture of substances of formulae (I) and (II) in molar proportions 4/1, in the form of an amorphous white powder in which the amino acids, determined with an auto-analyser after total hydrolysis occur in the following proportions:

Ala=1.27 (1); Glu=1.0 (1); Gly 1.0 (1); Dap=1.07 (1) (the closest whole number is indicated in parentheses).

The peptides (15 mg) thus obtained after filtration on Biogel P 2 were chromatographed on a Dowex 50×4 (100 cm×1.4 cm) column buffered at the start to pH 2.2 with pyridine: acetic acid-water (16:130:845 by volume) solvent adjusted to the desired pH with formic acid. With an elution gradient of 500 cm³, the pH being then 4.1, the tetrapeptide of formula (I) is obtained. It is purified by filtration over a column of Biogel P 2 by eluting with 240 cm³ of 0.01 M acetic acid.

In this way 7.5 mg of tetrapeptide of formula (I) is obtained. It has been verified by dansylation that this peptide indeed gives rise to equal amounts of dansyl-Gly and dansyl-Ala.

Figure 2:
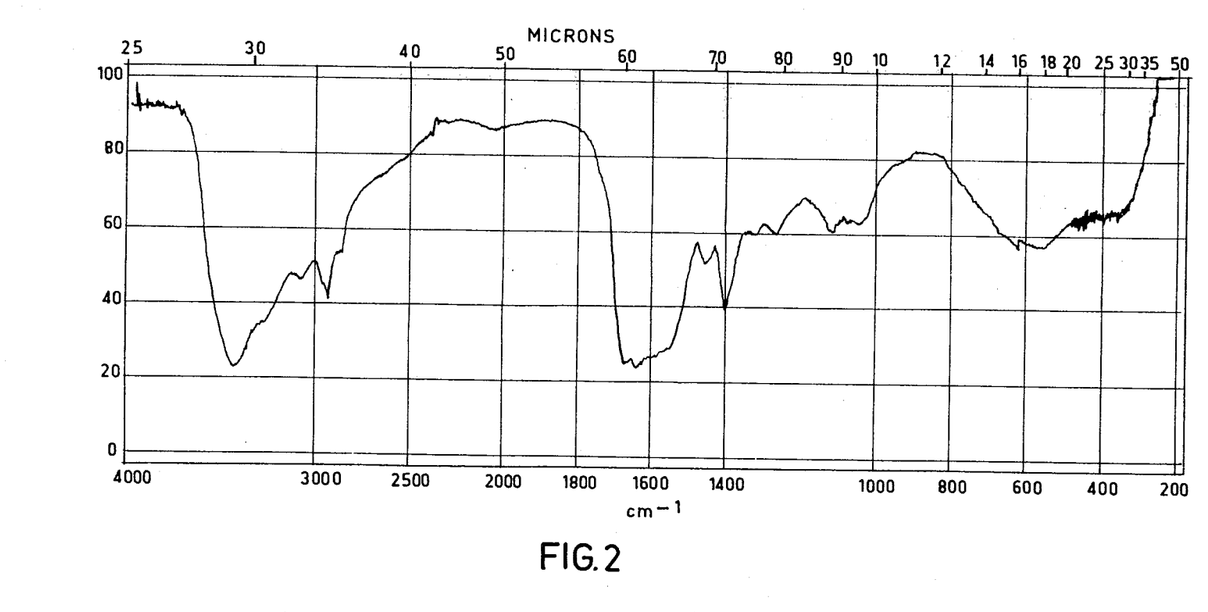

The IR spectrum of this substance is shown in FIG. 2.

The extract of *Streptomyces stimulosus* DS 25556 (NRRL 5776) denoted by the number 34129 R.P. can be prepared in the following way:

(a) Fermentation

Into a fermenter of 170 liters are charged:

| | |
|---|---|
| peptone | : 1200 g |
| yeast extract | : 600 g |
| glucose monohydrate | : 1200 g |
| partially hydrolysed starch | : 2400 g |
| tap water complement for 110 liters | |

The pH is adjusted to 7.30 by the addition of 40 cm³ of 10 N sodium hydroxide. The medium is sterilized by bubbling steam through at 122° C. for 40 minutes. After cooling, due to the fact of the condensation of the steam in the course of sterilization, the volume of the broth is 120 liters; the pH is 7.00. It is seeded with 200 cm³ of a culture in a shaken Erlenmeyer flask of *Streptomyces stimulosus* DS 25556. The culture is developed at 30° C. for 23 hours with shaking and aerating with sterile air; it is then suitable for the seeding of the production culture.

The production culture is carried out in a fermenter of 800 liters, charged with the following substances:

| | |
|---|---|
| corn steep (with 50% dry matter) | : 8 kg |
| soya oil | : 6 liters |

| | |
|---|---|
| ammonium sulfate | : 0.8 kg |
| cobalt chloride hexahydrate solution at 20 g/l | : 0.4 liter |
| tap water up to | : 360 liters |

After having adjusted the pH to 6.40 by the addition of 600 cm³ of 0.10 N sodium hydroxyde, there is added:

| | |
|---|---|
| calcium carbonate | : 2 kg |

The pH of the medium is then equal to 6.50. The medium is sterilized by bubbling steam through at 122° C. for 40 minutes. After cooling, due to the fact of the condensation of the steam in the course of the sterilization, the volume of the broth is 390 liters and it is made up to 400 liters by the addition of 10 liters of sterile aqueous solution containing:

| | |
|---|---|
| glucose monohydrate | : 4 kg |

The pH of the medium is then equal to 7.00. It is then seeded with 40 liters of the culture inoculum in a fermenter of 170 liters described above. The culture is developed at 27° C. for 71 hours, shaking with a rotary turbine at 205 rpm and aerating with a volume of 20 m³/h of sterile air; the pH of the culture is then 7.45 and the volume of the must is 380 liters.

(b) Isolation of the cells 100 l of the must obtained previously are continuously centrifuged to separate the cells under 3,000 g (4,000 rpm) and at the rate of 50 l. per hour.

In this way 6.4 kg of moist cells are collected. The cell paste is diluted in 20 l of ethanol. The insoluble product is isolated by centrifugation under 3,000 g (4,000 rpm) and at the rate of 25 l. per hour.

In this way 2.4 kg of wet cells are obtained which are taken up again in a mixture of 7 l of ethanol and 7 l of ethyl ether. The suspension is allowed to stand for 24 hours at a temperature of about 20° C.

The insolubles are separated by centrifugation under 3,000 g (4,000 rpm) and at the rate of 25 l. per hour and then dried under reduced pressure at 35° C. (5 mm of mercury).

In this way 852 g of *Streptomyces stimulosus* DS 25556 cells are isolated.

(c) Delipidation of the cells 750 g of dried cells of *Streptomyces stimulosus* DS 25556 are suspended in 6 l of chloroform and shaken for 24 hours at a temperature close to 20° C. After draining on a Buchner funnel provided with a filter paper, the chloroform is removed. The cells were then treated three times as previously. The isolated cells were dried under reduced pressure (5 mm of mercury) and at 35° C. In this way 690 g of delipidated *Streptomyces stimulosus* DS 25556 cells were obtained.

(d) Autolysis of the cells 30 g of the delipidated cells obtained as indicated previously were suspended in 500 cm³ of water containing 0.5 cm³ of toluene. The suspension was shaken for 48 hours at 37° C. and then it was centrifuged for 30 minutes at 15,000 g. The supernatent liquor was isolated for later treatment, and the cake suspended again in 500 cm³ of water and 0.5 cm³ of toluene and the suspension was shaken for 48 hours at 37° C. The supernatent liquor was isolated as previously, and the cake subjected a third time to autolysis under the same conditions, a third supernatent liquor being then isolated.

The three supernatent liquors obtained were subsequently treated by the same process and could be used together or separately.

(e) Treatment on ultrafiltration membrane 300 cm³ of the supernatent liquor obtained previously were ultrafiltered on an AMICON UM 20 membrane. The solution was first concentrated to about 100 cm³ and then was dialysed by 500 cm³ of water keeping a constant volume of 100 cm³. The retentate obtained was removed and the permeate was ultrafiltered on an AMICON UM 2 membrane to be first concentrated to about 100 cm³ and them dialysed by 1000 cm³ of water keeping the volume constant at 100 cm³.

The permeate was removed and the retentate was lyophilized. In this way 155 mg of water-soluble substance 34129 RP was obtained of which the characteristics were the following:
- elementary analysis:
$C\% = 40.4–41.4$ $H\% = 6.7–6.9$ $N\% = 8.0–10.6$
- composition:

(a) amino-acids: alanine (5–7%), glutamic acid (7–10%), glycine (2.5–4%), α,α-diaminopimelic acid (5–8%)

(b) amino-sugars: N-acetylglucosamine (5–10%), muramic acid (5–10%).

The present invention also relates to the pharmaceutical compositions which contain at least one compound according to the invention, in association with one or several diluents or compatible and pharmaceutically acceptable excipients. These compositions can be used as vaccine adjuvants (for example, antiinfluenza vaccine composed of hemagglutinating sub-units, antipolyomyelitic vaccine with inactivated virus, antimalarial vaccine) in simultaneous injection with the antigen (viral, bacterial, parasitic, fungal, tumoral) regarding which it is desirable to increase the antibody production or the specific cellular reactivity. Their adjuvant properties can also be exploited in desensitization processes against allergens (pollens, etc. . . ).

These pharmaceutical compositions can also be employed as non-specific immunostimulants in order to increase the resistance of the host (man or domestic animal) relative to infections, or in antitumoral immunotherapy.

As adjuvants, the products can be administered either in aqueous solution or in oil emulsion or again in the form of lyosomes with the antigen with regard to which it is desired to obtain an increased or improved immune response by the route utilized for this antigen (for example subcutaneous or intramuscular) and in proportions varying between 0.01 and 10 times the amount of antigen with which they are mixed before being injected.

For application as a non-specific immunostimulant, these products can be used by the intravenous, intramuscular, sub-cutaneous, intranasal, if necessary oral or rectal routes, either in aqueous solution, or in oily emulsion, or again in the form of lyposomes. In this case, the dose of the compound according to the invention which is administered is generally comprised between 0.01 and 25 mg/kg. In human therapeutics, the daily doses depend on the effect sought. They can be comprised between 0.1 and 10 mg for an adult.

As solid compositions for oral administration use may be made of tablets, pills, powders or granulates. In these compositions, the active product according to the invention is mixed with one or several diluents such as saccharose, lactose or starch. These compositions can also include other substances than the diluents, for example, a lubricant, such as magnesium stearate.

As liquid compositions for oral administration, it is possible to use pharmaceutically acceptable emulsions, solutions, suspensions, syrups or elixirs containing inert diluents, such as water or paraffin oil. These compositions can include substances other than diluents, for example wetting products, sweeteners or flavors.

The compositions for parenteral administration may be aqueous sterile solutions, suspensions or emulsions. As the vehicle, in the latter cases, it is possible to use polyethyleneglycol, propyleneglycol, vegetable oils, in particular olive oil, and injectable organic esters, for example, ethyl oleate. These compositions can also contain adjuvants, in particular wetting agents, emulsifiers or dispersing agents.

Sterilization can be effected in several ways, for example, by means of a bateriological filter, by incorporating sterilizing agents with the composition or by heating. They can also be prepared in the form of solid compositions rendered sterile by irradiation ($\beta$ rays) which can be dissolved in sterile water or dispersed in any other injectable sterile medium, if necessary at the time of use.

The compositions for intra-nasal administration may be aqueous sterile solutions, suspensions or emulsions which may be if necessary associated with a compatible propellant.

The compositions for rectal administration are suppositories which can contain, besides the active substance, excipients, such as cocoa butter or the product known under the name "suppo-cire".

The following example, given purely as a non-limiting example, illustrates a composition according to the invention.

EXAMPLE

The usual technique is used to prepare a solution administerable by the intravenous route and having the following composition:
- water-soluble substance prepared according to the invention, described in example 1: 50 mg
- injectable solvent 5 cm$^3$.

We claim:

1. Water-soluble compound selected from among the compounds corresponding to the following general formulae (III) and (IV) and their mixtures in molar proportions of about 4/1:

in which X represents a RCO radical and Y represents a hydrogen atom or a RCO radical, or again in which Y represents a RCO radical and X represents a hydrogen atom or a RCO radical, it being understood that, in these definitions, R represents an alkyl or alkenyl radical containing 11 to 19 carbon atoms in a straight or branched chain and in which the amino acids have the following configurations: Ala:L, Glu:D and Dap:LL.

2. Compound according to claim 1, wherein the RCO radical is the lauroyl radical.

3. Tetrapeptide selected from among the compounds corresponding to formulae (I) and (II) below and their mixtures in a molar ratio of about 4/1:

4. Method of treating human or animal subjects to stimulate immunological activity comprising administering a compound according to claim 1.

5. Method of treating human or animal subjects to stimulate immunological activity comprising administering a compound according to claim 2.

6. Pharmaceutical compositions useful in human or veterinary therapeutics, containing a pharmaceutically active material and as an immunological adjuvant an immunologically effective amount of at least one of the compounds according to claim 1.

7. Pharmaceutical compositions useful in human or veterinary therapeutics, containing a pharmaceutically active material and as an immunological adjuvant an immunologically effective amount of at least one of the compounds according to claim 2.

8. An immunologically effective composition useful in human and veterinary medicine comprising an immunologically effective amount of at least one compound of claim 1 in association with a pharmacologically acceptable diluent or excipient.

9. An immunologically effective composition useful in human and veterinary medicine comprising an immunologically effective amount of at least one compound of claim 2 in association with a pharmacologically acceptable diluent or excipient.

* * * * *

Disclaimer and Dedication 4,261,979.—*Pierre Jolles,* Paris; *Jean Florent,* Boulogne-Billancourt; *Jean Lunel,* Paris; *Denise Mancy,* Charenton and *Daniele Migliore-Samour,* Kremlin-Bicetre, France. NOVEL WATER-SOLUBLE COMPOUNDS DERIVED FROM EXTRACTS OF STREPTOMYCES STIMULOSUS, PROCESS FOR THEIR PRODUCTION, THEIR USES AS IMMUNOLOGICAL ADJUVANTS AND COMPOSITIONS CONTAINING THEM. Patent dated Apr. 14, 1981. Disclaimer and Dedication filed Apr. 30, 1984, by the assignee, *Acence Nationale De Valorisation De La Recherche (Anvar).*

Hereby disclaims and dedicates to the Public the entire term of said patent.
[*Official Gazette November 6, 1984.*]